United States Patent [19]

Peles

[11] Patent Number: 5,416,417
[45] Date of Patent: May 16, 1995

[54] METHOD AND SYSTEM FOR INVESTIGATING MASTITIS OF A COW BY MEASURING ELECTRICAL CONDUCTIVITY OF MILK

[75] Inventor: Eli Peles, Kibbutz Afikim, Israel

[73] Assignee: S.A.E. Afikim, Kibbutz Afikim, Israel

[21] Appl. No.: 875,064

[22] Filed: Apr. 28, 1992

[30] Foreign Application Priority Data

May 8, 1991 [IL] Israel ......................................... 98081

[51] Int. Cl.⁶ ............................................. G01N 27/06
[52] U.S. Cl. .................................................. 324/439
[58] Field of Search ........................ 324/439, 444, 425

[56] References Cited

U.S. PATENT DOCUMENTS

| | | | |
|---|---|---|---|
| 3,664,306 | 5/1972 | Quayle et al. | 324/443 X |
| 4,156,179 | 5/1979 | Stephen et al. | 324/442 |
| 4,325,028 | 4/1982 | Takahashi | 324/442 |
| 4,771,007 | 9/1988 | Tippetts et al. | 324/450 X |

FOREIGN PATENT DOCUMENTS 1494831 2/1975 United Kingdom .
1438281 6/1976 United Kingdom .

Primary Examiner—Kenneth A. Wieder
Assistant Examiner—Glenn W. Brown
Attorney, Agent, or Firm—Helfgott & Karas

[57] ABSTRACT

A method for investigating an electrical conductivity of milk from an individual cow, comprising the steps of measuring at least one electrical conductivity of at least one daily milking on each of a plurality of successive days and storing the respective electrical conductivities or computed functions thereof. An average value of the electrical conductivities or of functions thereof is then computed and stored for the preceding x days but excluding the previous y days where y<x, and at least once each day any deviation between the electrical conductivity or function thereof and the average stored value is determined. The deviation is stored and/or displayed and serves as an indication of the onset of mastitis. A system for carrying out the method is also disclosed.

9 Claims, 2 Drawing Sheets

METHOD AND SYSTEM FOR INVESTIGATING MASTITIS OF A COW BY MEASURING ELECTRICAL CONDUCTIVITY OF MILK

FIELD OF THE INVENTION

This invention relates to a method and system for investigating an electrical conductivity of milk from an individual cow. In particular it relates to such a method and system for predicting a likely onset of mastitis in the cow being investigated.

BACKGROUND OF THE INVENTION

The correlation between milk mastitis and electrical conductivity of the milk is well established. There exist many references in both the scientific and patent literature for determining the presence of mastitis from measured electrical conductivities of a cow's milk. Thus, for example, British Patent No. 1 438 281 describes a mastitis detector based on the electrical conductivity of a cow's milk and comprising an improved conductivity cell.

British Patent No. 1 494 831 is directed to a method and apparatus for the early detection of mastitis, for example, whilst in the sub-clinical stage enabling corrective action to be taken before the infection has any significant effect upon the quality or quantity of milk yield. The method disclosed in the above-mentioned patent is based on the finding that in practically all cases of mastitis the level of infection is different in at least two of the four teats of a cow for at least a period of time equal to that between successive milkings. Based on this fact, a comparison of the impedance of the milk drawn from each teat at each milking is used to detect the onset of mastitis.

It is further stated that the constant monitoring to detect mastitis may also serve to detect general infection of a cow by comparing the individually measured conductivities with a reference conductivity corresponding to a norm derived from a sample of pure milk from a healthy cow. It is thus suggested that the onset of mastitis in a cow may be determined with reference to the milk conductivities associated with a different, healthy cow.

Similarly, U.S. Pat. No. 4,325,028 analyzes the conductivities of milk drawn from quarter mammae by subtracting the minimum conductivity of the four mammae from the conductivities associated with the remaining three. The resulting differential conductivities are compared with predetermined reference values, mastitis being indicated when any one differential value is greater than an upper threshold. In a practical system, the differential conductivities are compared with a lower threshold of $5 \times 10^{-4}$ S/cm the higher threshold being $15 \times 10^{-4}$ S/cm, no support being given in the referenced patent for either of these figures.

Underlying the methods employed in the above-mentioned prior art references is an assumption that there is some normal value of electrical conductivity which may be used as a yardstick against which the milk conductivities associated with individual cows may be compared in order to assess the onset of mastitis. It has been found, however, that this basic assumption is too simplistic to provide meaningful data in anything but clear-cut cases of mastitis. Thus, for example, whilst the above-mentioned global conductivities of 5 and 15 m℧/cm can indeed be used as an indication that a measured sample of milk is mastitic, they are too broad to permit prediction of mastitis or to indicate the onset of mastitis in its incipient stages.

It is obviously desirable to predict the likely onset of mastitis, if possible, so that suitable remedial action can be taken and the cow restored to full health without incurring the inevitable loss of milk yield which accompanies mastitis. However, the prior art is concerned only with improved systems for measuring electrical conductivity or for methods which establish mastitis once it has already occurred, no method having yet been suggested for analyzing electrical conductivity data so as to predict the likely onset of mastitis.

It is, in fact, difficult to define criteria which predict the onset of mastitis for the following reasons:

1. the electrical conductivity of a cow's milk does not remain constant even throughout the same milking;
2. the electrical conductivity associated with a cow's milk varies throughout the day so that, for example, the conductivity of the morning milking may well be different from that of the evening milking;
3. the conductivity of the cow's milk depends on factors apart from the general health of the cow such as, for example, the kind of feed consumed by the cow, ambient conditions such as climate, and so on;
4. the conductivity of a cow's milk increases towards the end of the cow's lactation; and
5. the milk conductivity associated with a healthy cow lies within the range 9–15 m℧/cm. This range is sufficiently broad that significant fluctuations in the electrical conductivity of an individual cow's milk can occur within this range without the cow being classified as unhealthy.

SUMMARY OF THE INVENTION

It is an object of the invention to provide a method and system for investigating an electrical conductivity of milk from an individual cow which permits the likely onset of mastitis to be gauged with greater certainty than provided in hitherto proposed methods.

According to a broad aspect of the invention there is provided a method for investigating an electrical conductivity of milk from an individual cow, comprising the steps of:

(a) measuring at least one electrical conductivity of at least one daily milking on each of a plurality of successive days and storing the respective electrical conductivities or computed functions thereof, (b) computing and storing an average value of the electrical conductivities or functions thereof stored in (a) for the preceding x days but excluding the previous y days where $y < x$, (c) at least once each day computing any deviation between the electrical conductivity or computed function thereof determined in (a) and the average value computed and stored in (b), and (d) storing and/or displaying any deviation computed in (c).

Thus, the method according to the invention does not rely on global conductivities which, precisely because they must be relevant to large numbers of different cows, cannot be sufficiently fine-tuned to permit the prediction of mastitis for a specific cow before it has actually occurred. Rather, the method according to the invention relies on specific thresholds being established for each individual cow based on the recent history of measured conductivities, any significant offset therefrom being used as an early predictor of mastitis.

BRIEF DESCRIPTION OF THE DRAWINGS

The invention will now be described, by way of non-limiting example only, with regard to a method for investigating an electrical conductivity of milk from an individual cow and with reference to the accompanying drawings, in which.

DETAILED DESCRIPTION OF A PREFERRED EMBODIMENT

The method and system according to the invention are not concerned with the actual manner in which electrical conductivity is measured it being merely understood that means are provided for determining the electrical conductivity of a cow's milk and for storing the measured values. The above-mentioned prior art references all show systems for measuring the electrical conductivity of a cow's milk and their disclosures are therefore incorporated herein by reference.

Figure 1:
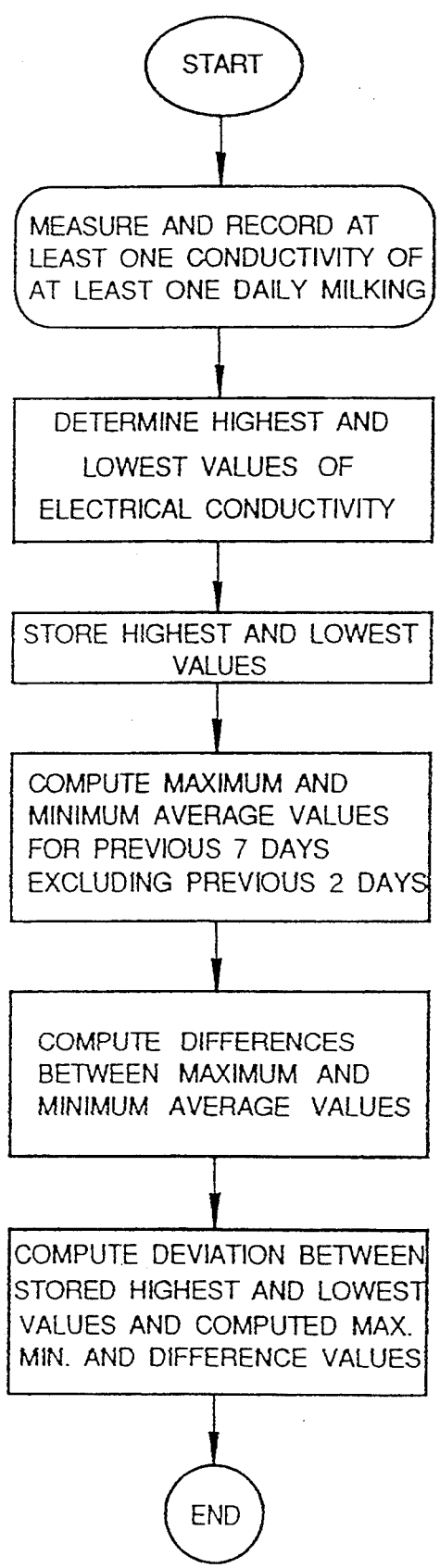
FIG. 1 is a flow diagram showing the principal steps in a method according to the invention.

FIG. 1 shows the principal steps for investigating an electrical conductivity of milk from an individual cow of which the first step is the measurement of at least one electrical conductivity of at least one daily milking in respect of each cow being investigated. Typically, a cow is milked in the morning, the afternoon and again in the evening and the electrical conductivities of the milk during each milking is constantly monitored so as to determine the highest and lowest values of electrical conductivity associated with each milking. Each of these values is then stored for subsequent processing. From the stored highest and lowest conductivity values, the maximum and minimum average values are computed for each of the previous seven days except the preceding two days and the differences between the maximum and minimum average values are likewise computed.

This having been done, any deviation between the stored highest and lowest conductivity values for the current milking from the computed maximum, minimum and difference values is computed and stored.

The stored deviations give an indication of the general state of health of the individual cow based on that cow's recent history and thus permit the onset of mastitis to be predicted. For example, a 15% deviation of the highest electrical conductivity value associated with a particular milking from the computed maximum average value as calculated for the previous seven days has been shown to provide a very good indication of the onset of mastitis.

It should be noted that, when calculating the maximum and minimum average values, the preceding two days are excluded from the computation so that any change in conductivity during the previous two days owing, for example, to the onset of mastitis, will not affect the average which is, in effect, the yardstick against which the general good health of the cow is judged.

In the preferred embodiment, the averaging is performed over a cycle of seven days, it having been found that if too long a cycle is considered the average values do not reliably reflect fluctuations in milk conductivity owing to climatic fluctuations, changes in feed and other physical changes not directly associated with the cow's physical health.

Figure 2:
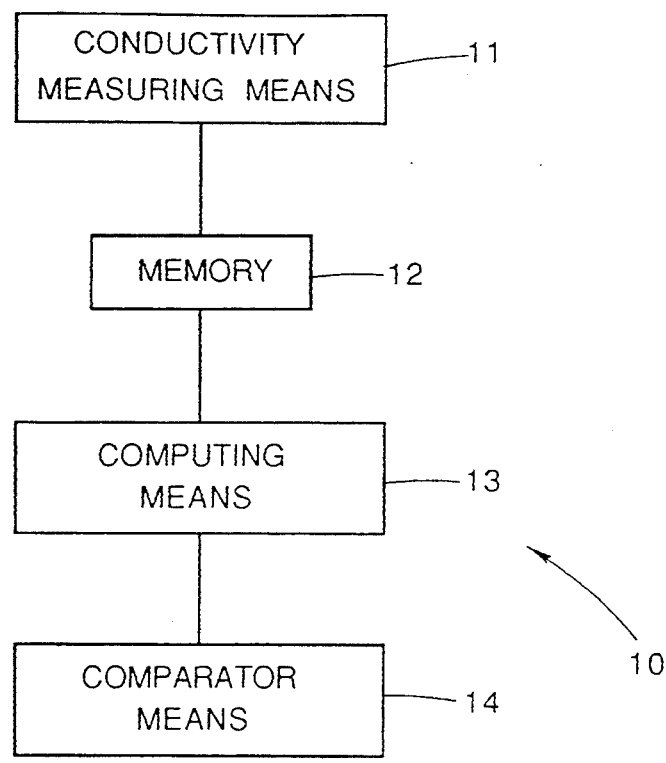
FIG. 2 is a block diagram depicting a system for performing the method according to the invention.

Referring now to FIG. 2 of the drawings, there is shown a system designated generally as 10 for carrying out the method described above. The system 10 includes conductivity measuring means 11 for measuring the electrical conductivities of a cow's milk, the measured values being stored in a memory 12. Coupled to the memory 12 is a computing means 13 having coupled thereto a comparator means 14 for processing the measured values of conductivities stored in the memory 12 in accordance with the detailed method steps described above. It will be understood that the average values over the period of the previous seven days can be stored for subsequent processing or, alternatively, they can be calculated from the stored conductivity data as required. In the latter case, the processing time is slightly longer but the capacity of the memory 12 is smaller.

Although in FIG. 2, the comparator means 14 is depicted as a separate unit to the computing means 13, it will clearly be understood that both functions may be provided as an integral unit.

Thus, the invention permits the determination of a normative electrical conductivity or function thereof for each individual cow, any significant deviation from which is then used as a primary indicator of the onset of mastitis. This is quite distinct from hitherto proposed methods which have suggested the use of a normative electrical conductivity value (or range thereof) equally applicable to all cows or populations of cows and which are, therefore, necessarily too broad to permit accurate prediction of mastitis before its actual onset.

Whilst the specific time cycles described in the preferred embodiment have been shown experimentally to provide good predictions of the onset of mastitis, it will be appreciated that these figures can be varied according to individual needs without departing from the spirit of the invention.

I claim:

1. A method for investigating an electrical conductivity of milk from an individual cow, comprising the steps of:
   (a) measuring at least one electrical conductivity of at least one daily milking from the individual cow on each of a plurality of successive days and storing the respective electrical conductivities or computed functions thereof,
   (b) storing an average value of the electrical conductivities or functions thereof stored in (a) for the preceding x days but excluding the previous y days where $y<x$,
   (c) at least once each day determining any deviation between the electrical conductivity or computed function thereof determined in (a) and the average value stored in (b) and
   (d) storing and/or displaying any deviation determined in (c) so as to predict an onset of mastitis in the cow if said deviation differs from a predetermined value.

2. The method according to claim 1, wherein $x \geq 7$ and $y \geq 2$.

3. The method according to claim 2, wherein said computed functions include a highest and lowest measured conductivity.

4. The method according to claim 3, wherein a deviation of approximately 15% determined in (c) constitutes a first indication of an onset of mastitis.

5. The method according to claim 2, wherein a deviation of approximately 15% determined in (c) constitutes a first indication of an onset of mastitis.

6. The method according to claim 1, wherein said computed functions include a highest and lowest measured conductivity.

7. The method according to claim 6, wherein a deviation of approximately 15% determined in (c) constitutes a first indication of an onset of mastitis.

8. The method according to claim 1, wherein a deviation of approximately 15% determined in (c) constitutes a first indication of an onset of mastitis.

9. A system for investigating an electrical conductivity of milk from an individual cow, the system comprising:

- a measuring unit for measuring an electrical conductivity of milk from the individual cow on each of a plurality of successive days,
- a memory coupled to the measuring unit for storing therein measured values of electrical conductivity,
- a computer unit coupled to the memory for determining an average value of the stored electrical conductivities or of a function thereof, and
- a comparator coupled to the memory and to the computer unit for comparing the average value or function thereof with the respective value or function thereof to determine any deviation between the electrical conductivity or function thereof measured by said measuring unit and the average value determined in said computer unit so as to predict an onset of mastitis in the cow if said deviation differs from a predetermined value.

* * * * *